(12) United States Patent
Morgan (10) Patent No.: US 9,447,915 B1
(45) Date of Patent: Sep. 20, 2016

(54) METHODS AND APPARATUS FOR SEISMIC MOUNT

(71) Applicant: Brent Morgan, Glendale, AZ (US)

(72) Inventor: Brent Morgan, Glendale, AZ (US)

(*) Notice: Subject to any disclaimer, the term of this patent is extended or adjusted under 35 U.S.C. 154(b) by 0 days.

(21) Appl. No.: 15/077,735

(22) Filed: Mar. 22, 2016

(51) Int. Cl.
| | | |
|---|---|---|
| *F16M 11/00* | (2006.01) | |
| *F16M 13/00* | (2006.01) | |
| *A61B 90/50* | (2016.01) | |
| *F16M 13/02* | (2006.01) | |
| *E04B 1/98* | (2006.01) | |
| *F16F 7/08* | (2006.01) | |
| *F16M 11/20* | (2006.01) | |
| *F16M 11/08* | (2006.01) | |

(52) U.S. Cl.
CPC .............. *F16M 13/02* (2013.01); *E04B 1/985* (2013.01); *F16F 7/08* (2013.01); *F16M 11/2014* (2013.01); *A61B 90/50* (2016.02); *F16F 2222/04* (2013.01); *F16F 2224/02* (2013.01); *F16F 2230/0023* (2013.01); *F16M 11/08* (2013.01); *F16M 13/027* (2013.01); *F16M 2200/041* (2013.01)

(58) Field of Classification Search
CPC .. A61B 90/50; F16M 11/08; F16M 11/2014; F16M 13/02; F16M 13/027; F16M 2200/041
USPC ................ 248/562, 610, 638, 317, 233, 327
See application file for complete search history.

(56) References Cited

U.S. PATENT DOCUMENTS

| | | | | |
|---|---|---|---|---|
| 4,083,522 A | * | 4/1978 | Vandersip | F16L 3/2053 248/59 |
| 4,200,256 A | | 4/1980 | Thiel | |
| 4,371,141 A | | 2/1983 | Baratoff | |
| 5,009,386 A | * | 4/1991 | Berger | F16L 3/2053 248/59 |
| 5,456,047 A | * | 10/1995 | Dorka | F16F 7/082 248/568 |
| 5,487,524 A | * | 1/1996 | Bergetz | F16F 15/085 248/343 |
| 6,364,268 B1 | * | 4/2002 | Metelski | F16M 11/04 248/317 |
| 6,817,585 B2 | * | 11/2004 | Wagner | F16M 11/04 248/324 |
| 7,028,969 B2 | | 4/2006 | Meisel et al. | |
| 8,091,849 B2 | | 1/2012 | Ayadhi | |
| 8,322,674 B2 | | 12/2012 | Metelski | |
| 2010/0053589 A1 | * | 3/2010 | Hashemi | F16F 15/06 355/77 |
| 2011/0147563 A1 | * | 6/2011 | Metelski | F16M 11/08 248/610 |

* cited by examiner

*Primary Examiner* — Tan Le
(74) *Attorney, Agent, or Firm* — The Noblitt Group, PLLC (57) ABSTRACT

A seismic mount according to various aspects of the present technology may comprise a housing having at least two independent isolation sections. The first isolation section may comprise a sliding plate system fixedly attached to a structure on a first end and disposed within the housing on a second end. The first sliding plate may be configured to allow the housing to move about the fixed position of the first sliding plate during a transient period such as seismic event. A second sliding plate system may be coupled to the housing and extend downwardly therefrom. The second sliding plate system may be configured to allow for independent movement of both the housing and the second sliding plate system with respect to each other during the seismic event.

18 Claims, 5 Drawing Sheets

METHODS AND APPARATUS FOR SEISMIC MOUNT

BACKGROUND OF THE TECHNOLOGY

Seismic isolators are used to restrain equipment to a structure during transient events that might damage the equipment or cause the equipment to fall or tip over potentially causing harm to nearby persons. Traditional overhead isolators rely on various types of pivots, springs, and vibration dampeners directed at trying to reduce the transfer of loads from the structure to the equipment. For example, a ball joint has been used in an attempt to allow the suspended equipment to rotate about a fixed pivot point attached to the structure. This may reduce certain types of transferred loads to the equipment but the equipment may be left to swing or oscillate causing damage to the equipment or surrounding structures. Other devices have attempted to use traditional isolation devices such as compressible springs or pads to absorb forces rather than transfer those loads to the equipment. Although prior art seismic isolators work to some degree, their effectiveness can be limited or they may be difficult to install and adjust. Improper installation may further reduce the effectiveness of these isolators.

SUMMARY OF THE TECHNOLOGY

A seismic mount according to various aspects of the present technology may comprise a housing having at least two independent isolation sections. The first isolation section may comprise a sliding plate system fixedly attached to a structure on a first end and disposed within the housing on a second end. The first sliding plate may be configured to allow the housing to move about the fixed position of the first sliding plate during a transient period such as seismic event. A second sliding plate system may be coupled to the housing and extend downwardly therefrom. The second sliding plate system may be configured to allow for independent movement of both the housing and the second sliding plate system with respect to each other during the seismic event.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of hardware or software components configured to perform the specified functions and achieve the various results. For example, the present technology may employ various materials, connectors, and the like, which may carry out a variety of functions. In addition, the present technology may be practiced in conjunction with any number of suspension systems, and the system described is merely one exemplary application for the technology. Further, the present technology may employ any number of conventional techniques for dissipating energy, isolating movement, supporting loads, and the like.

Methods and apparatus for a seismic mount according to various aspects of the present technology may operate in conjunction with any suitable device for suspending equipment from a ceiling or other overhead structure. Various representative implementations of the present technology may be applied to any system for holding and isolating equipment from vibrations or movement that could be caused from movement of the structure itself. Certain representative implementations may include, for example, suspending medical equipment from a ceiling, isolating sensitive equipment from vibrations, and reducing transferred loads to suspended equipment.

Figure 1:
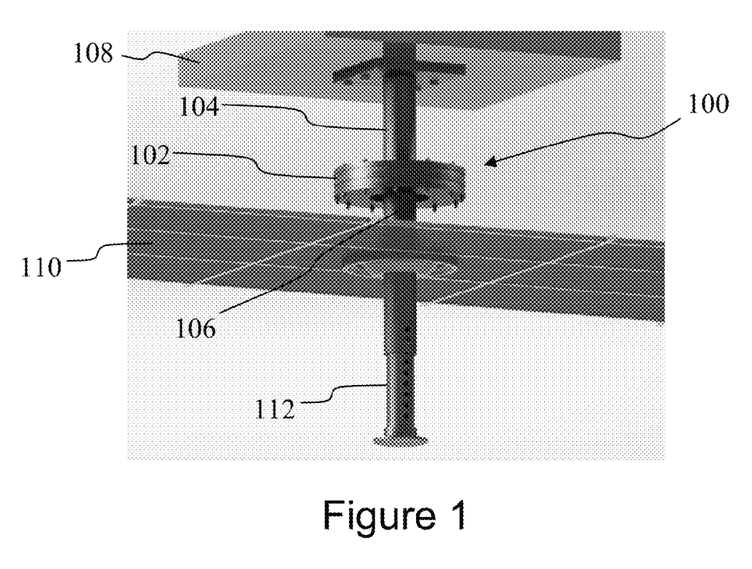
FIG. 1 representatively illustrates a perspective view of a seismic mount in accordance with an exemplary embodiment of the present technology.
Figure 2:
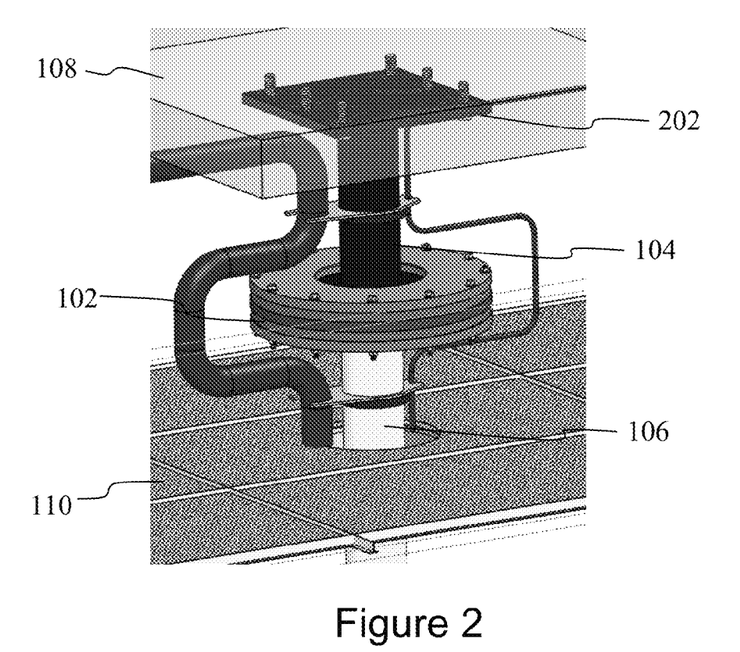
FIG. 2 representatively illustrates a close up view of an installed seismic mount in accordance with the present technology.
Figure 3:
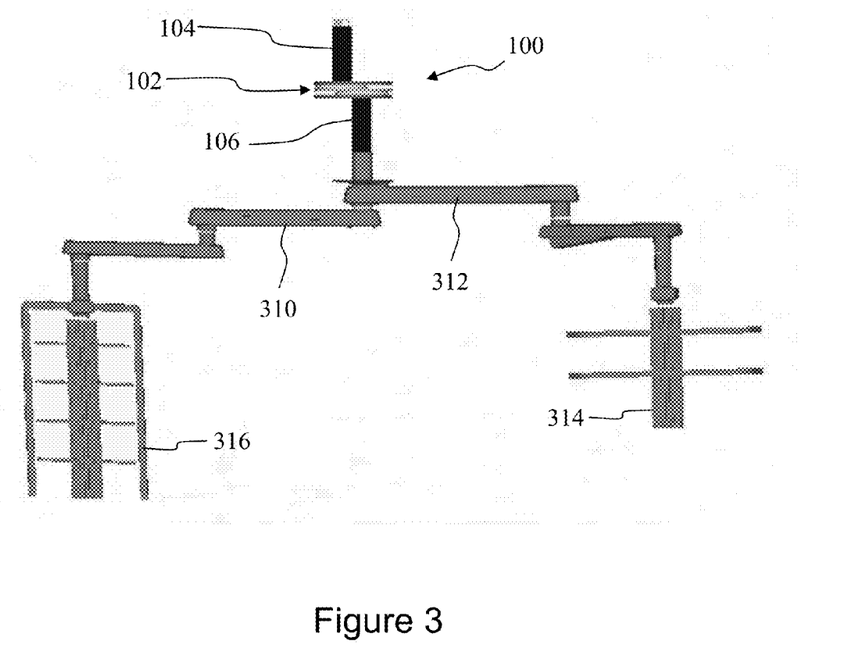
FIG. 3 representatively illustrates a side view of the seismic mount coupled to a pair of booms and equipment in accordance with an exemplary embodiment of the present technology.

Referring now to FIGS. 1-3, a seismic mount 100 according to various aspects of the present technology may comprise a housing 102 configured to be coupled to an overhead structure 108 by an upper pole 104. The housing 102 may further be configured to suspend at least one piece of equipment 314, 316 from a boom 310, 312 coupled to a lower pole 106 extending downwardly from the housing 102.

The housing 102 reduces an amount of vibrational loading that may be transferred to the at least one piece of equipment 314, 316 from the structure 108 over a transient period of time, such as during a seismic event. Referring now to FIGS. 4A-5B, the housing 102 may comprise a series of stacked plates arranged to generally decouple the lower pole 106 from the upper pole 104. For example, in one embodiment, the housing 102 may comprise an upper plate 402 coupled to a lower plate 406. The upper plate 402 may be separated from the lower plate 406 by at least one ring 408, 410. In addition, a middle plate 404 may be positioned between the upper and lower plates 402, 406 to create one or more internal regions within the housing 102 used to reduce the transfer of forces from the upper pole 104 to the lower pole 106.

Figure 4A:
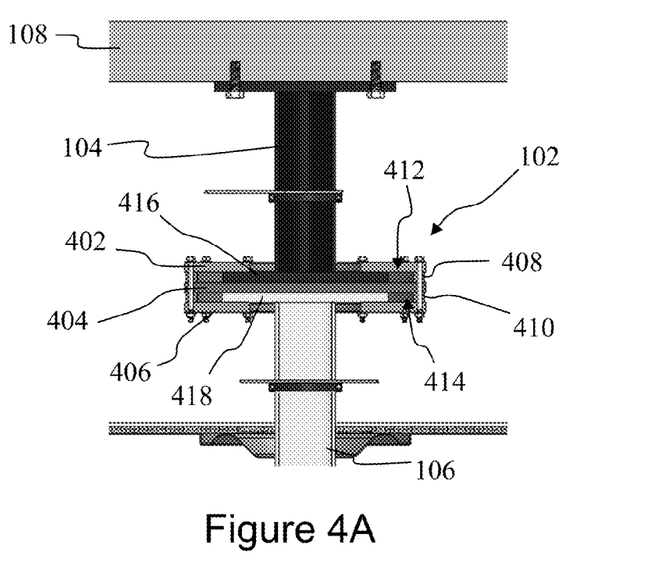
FIG. 4A representatively illustrates a cross-sectional view of the seismic mount in a neutral position in accordance with an exemplary embodiment of the present technology.
Figure 5A:
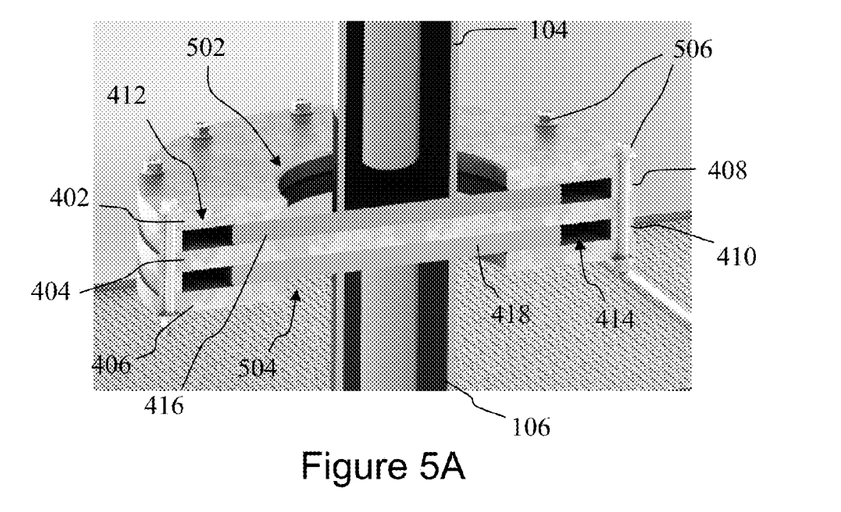
FIG. 5A representatively illustrates a perspective cross-sectional view of the seismic mount in the neutral position in accordance with an exemplary embodiment of the present technology.

The upper plate 402 may form an upper surface of the housing 102 and be suitably configured to allow the upper pole 104 to be received within the housing 102. For example, in one embodiment, the upper plate 402 may comprise a generally annular shape (donut) having an open center portion 502 to allow the upper pole to be received within an interior portion of the housing 102.

The upper plate 402 may comprise any suitable material such as metal, composite, polymer, and the like. The upper plate 402 may also be configured in any suitable size or dimension. For example, the dimensions of the upper plate 402 may be determined according to the type or weight of the equipment to be suspended from the structure 108. In one embodiment, the upper plate 402 may comprise steel or another metal alloy of between about one-eighth of an inch and about one inch thickness and having an outer diameter of between about six inches and twenty-four inches.

The open center portion 502 may similarly comprise any suitable dimension and may be selected according to a desired amount of allowed movement of the housing 102 relative to the upper pole 104. For example, the open center portion 502 may comprise a diameter of between about two inches and about twelve inches.

At least one surface of the upper plate 402 may also be configured to provide a desired coefficient of friction to help control the relative movement between the housing 102 and the upper pole 104. For example, in one embodiment, a lower surface of the upper plate 402 may comprise a coating selected to provide a specific friction level to help limit movement until a threshold force is applied to the structure 108, upper pole 104, or the housing 102 to overcome the frictional force.

The coating may comprise any suitable material or surface treatment to the lower surface that is selected to increase or decrease the coefficient of friction of the surface. In one embodiment, the coating may comprise a machine operation applied to the lower surface to create a non-uniform surface to help increase the coefficient of friction of lower surface of the upper plate 402. In an alternative embodiment, the coating may comprise an application of a chemical or material to the surface. For example, the coating may comprise a fluoropolymer such as: polyvinylfluoride; perfluoroalkoxy polymer; polytetrafluoroethylene; polytetrafluoroethylene; fluorinated ethylene-propylene; and the like applied to the lower surface of the upper plate 402. In yet another embodiment, the coating may comprise a sheet coupled to the lower surface of the upper plate 402 such as by welding, adhesively, or a mechanical fastener.

The lower plate 406 may form a lower surface of the housing 102 and be suitably configured to allow the lower pole 106 to be received within and extend downwardly from the housing 102. The lower annular plate 405 may be configured substantially identical to the upper plate 402 and may comprise a generally circular plate having a second open center portion 504 to allow the lower pole to be received within the interior portion of the housing 102. In a similar as the upper plate 402, an upper surface of the lower plate 406 may be configured with a desired coefficient of friction to help control the relative movement between the housing 102 and the lower pole 106.

The middle plate 404 may be disposed within the housing 102 and positioned between the upper plate 402 and the lower plate 406. The middle plate 404 may comprise a generally circular plate constructed substantially similar the upper annular and lower annular plates 402, 406 but without an open center portion. Dimensions of the middle plate 404 may also be substantially the same as the upper annular and lower annular plates 402, 406 though a thickness of the middle plate 404 may be adjusted to help provide additional rigidity or overall strength to the housing 102 if needed to support a given load.

At least one surface of the middle plate 404 may be configured with a desired coefficient of friction to help control the relative movement of the upper and lower poles 104, 106. For example, in one embodiment, both an upper and a lower surface of the middle plate 404 may comprise a coating selected to provide a specific friction level to help control movement of the housing relative to the upper and lower poles 104, 106. The coating may be identical to those used for the upper and/or lower annular plates 402, 406 or the coating used on the middle plate 404 may be different if necessary to provide a desired coefficient of friction due to the varying forces applied to the surfaces. For example, due to gravity, the upper surface of the middle plate 404 may be subjected to a slightly higher force than the lower surface of the middle plate 404. As a result of this difference, it may be necessary for the upper surface of the middle plate 404 to have a different coefficient of friction than the lower surface of the middle plate 404 to better provide a desired level of isolation or dampening during the transient period of time.

The middle plate 404 may be separated from the upper and lower plates 402, 406 by at least one ring 408, 410 to form at least one interior volume 412, 414 within the housing 102 for receiving at least one slideable plate 416, 418. The rings 408, 410 may comprise any suitable system or device for separating the middle plate 404 from the upper and lower plates 402, 406 such as a spacer, block, gasket, isolation element, and the like. In one embodiment, the rings 408, 410 may comprise a metallic ring of between about one-eighth of an inch and about one inch thickness and have an outer diameter of between about six inches and twenty-four inches to match the outer dimensions of the upper and lower plates 402, 406. An inner diameter of the rings 408, 410 may be larger than the diameter of the first and second open center portions 502, 504.

The thickness and dimensions of the rings 408, 410 may be determined according to any suitable criteria such as to control the size of the at least one interior volume within the housing 102. For example, a first interior volume 412 may be defined by the lower surface of the upper plate 402, a first ring 408, and an upper surface of the middle plate 404. Similarly, a second interior volume may be defined by an upper surface of the lower plate, the second ring, and a lower surface of the middle plate. For example, the rings 408, 410 may comprise a width of between about one-half of an inch and about two inches such that first and second interior volumes 412, 414 have a larger inner diameter than that of the first and second open center portions 502, 504.

A first sliding plate 416 may be positioned within the first interior volume 412 and be configured to couple to the upper pole 104. The first sliding plate 416 may comprise any suitable device for allowing the housing 102 to move with respect to the upper pole that is fixedly attached to the structure 108. The first sliding plate 416 may be coupled to the upper pole 104 by any suitable method or the first sliding plate 416 and the upper pole 104 may be formed integrally as a single piece.

The first sliding plate 416 may comprise any suitable material such as metal, composite, or polymer that may be selected according to any desired criteria such as the ability to move or slide against the surfaces of the upper and middle plates 402, 404. The first sliding plate 416 may also comprise a surface treatment similar to that described above for the upper, middle, and lower plates 402, 404, 406 to control the coefficient of friction of the first sliding plate 416.

Figure 6A:
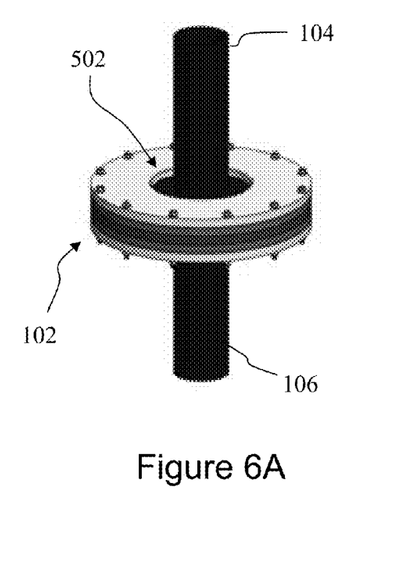
FIG. 6A representatively illustrates a perspective view of the seismic mount in the neutral position in accordance with an exemplary embodiment of the present technology.

The first sliding plate 416 may be constructed similarly to the upper, middle, and lower plates 402, 404, 406 except that the first sliding plate 416 may comprise dimensions allowing it to slide or otherwise move within the first interior volume 412. For example, referring now to FIGS. 4A, 5A, and 6A, the first sliding plate 416 may be initially centered in the first open center portion 502 such that the first sliding plate 416 is substantially centered within the first interior volume 412. The first sliding plate 416 may also be fixed in position as a result of being coupled to the structure 108 by the upper pole 104.

Figure 4B:
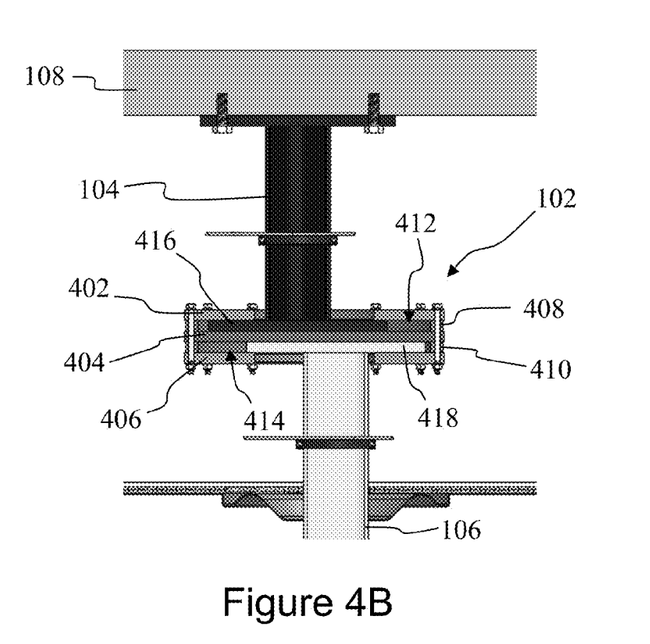
FIG. 4B representatively illustrates a cross-sectional view of the seismic mount in an offset position in accordance with an exemplary embodiment of the present technology.
Figure 5B:
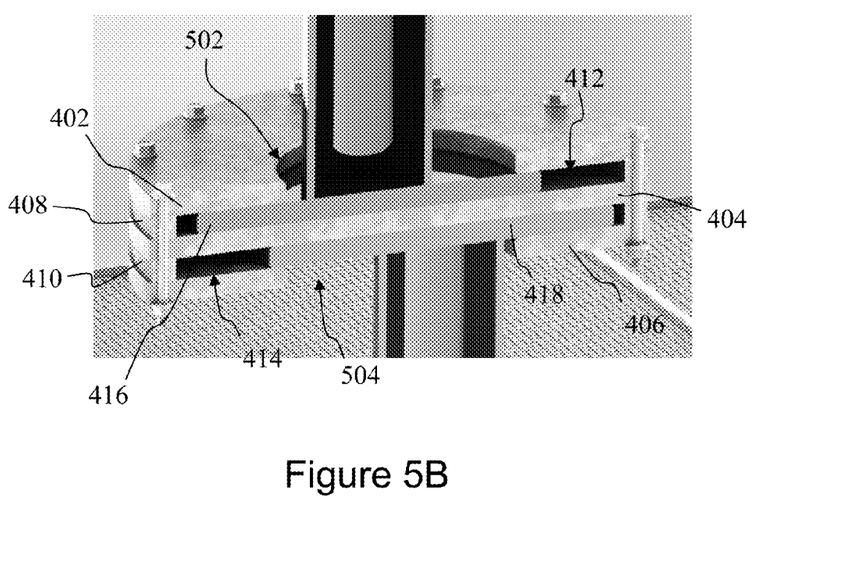
FIG. 5B representatively illustrates a perspective cross-sectional view of the seismic mount in an offset position in accordance with an exemplary embodiment of the present technology.
Figure 6B:
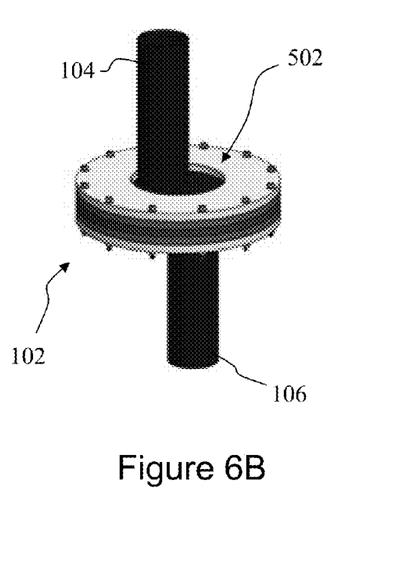
FIG. 6B representatively illustrates a perspective view of the seismic mount in the offset position in accordance with an exemplary embodiment of the present technology.

Referring now to FIGS. 4B, 5B, and 6B, during a seismic event, the housing 102 may shift, slide, or otherwise move from its initial position with respect to the first sliding plate 416 as a result of the structure 108 moving from the seismic event. This relative movement of the housing 102 has the effect of at least partially decoupling or isolating the housing 102 from the structure 108 thereby reducing any lateral or shear forces that would have been transferred to the equipment 314, 316.

Referring again to FIGS. 4A, 5A, and 6A, a second sliding plate 418 may be positioned within the second interior volume 414 and be configured to couple to the lower pole 106. The second sliding plate 418 may comprise any suitable device for allowing the housing 102 to move with respect to the lower pole 106 that is attached to the equipment 314, 216. The second sliding plate 418 may be coupled to the lower pole 106 by any suitable method or the second sliding plate 416 and the lower pole 106 may be formed integrally as a single piece.

The second sliding plate 418 may be constructed similarly as the first sliding plate 416. The second sliding plate 418 may also be configured to perform in a similar fashion to the first sliding plate 416. For example, second sliding plate 418 may be initially centered in the second open center portion 504 such that the second sliding plate 418 is substantially centered within the second interior volume 414. Referring now to FIGS. 4B, 5B, and 6B, during a seismic event, the second sliding plate 418 may shift, slide, or otherwise move from its initial position with respect to the housing 102 as a result of the structure 108 moving from the seismic event. This relative movement of the second sliding plate 418 has the effect of providing additional decoupling or isolation of the equipment 314, 316 from the structure 108 to further reduce any lateral or shear forces that would have been transferred to the equipment 314, 316.

The first and second sliding plate 416, 418 may be configured to move within the housing 102 by any suitable direction or amount. In one embodiment, the first and second open center portions 502, 504 may comprise a generally circular shape suitably configured to allow the upper and lower pole 104, 106 to move in a 360 degree range of motion within the limits of the area formed by the respective first and second open center portions 502, 504. For example, if the first open center section 502 comprises a diameter of about five inches, then the upper pole 104 and the housing 102 may have up to five inches of relative movement in any direction with respect to each other.

The housing 102 may further comprise a limiter such as a block or safety tab (not shown) configured to limit movement of at least one of the upper and lower pole 104, 106 within the respective first and second open center portions 502, 504. In one embodiment, the limiter may be coupled to the lower pole 106 and/or the second sliding plate 418 and be configured to limit movement of the second sliding plate 418 to a smaller range of motion within the second open center portion 504 unless a threshold force is applied to the housing 102. The limiter may comprise a block configured to yield under a predetermined force that exceeds the required force to simply overcome the coefficient of friction between the second sliding plate 418 and the middle and lower annular plates plate 404, 406. For example, the limiter may be positioned within the second interior volume 414 to limit movement of the second sliding plate to about fifteen to twenty-five percent of the total diameter of the second open center portion 504. This would allow the second pole 106 to be moved or adjusted slightly to accommodate installation or use requirements. During a seismic event the housing 102 may be subjected to forces large enough to cause the second sliding plate 418 to move into the limiter with at the threshold force such that the second sliding plate 418 may then be allowed to move within the entire range allowed by the second open center portion 504.

The components making up the housing 102 may be coupled together by any suitable method such as by welding, mechanical fastener, or adhesively. Referring now to FIG. 5A, in one embodiment a plurality of bolts 506 may be used to couple the upper plate 402, the first ring 408, the middle plate 404, the second ring 410, and the lower plate 406 together. The connection method may also be used to help control and/or adjust the ability of the first and second sliding plates 416, 418 to slide within the housing 102. For example, the bolts 506 may be tightened to a specific torque value to provide a desired compression force between the upper, middle, and lower plates 402, 404, 406. A higher compression force may be used to increase the force required to overcome the coefficient of friction between the sliding plates 416, 418 and the inner surface of the respective interior volumes 412, 414. Similarly, a lower compression force may be used to decrease the force required to cause the first and second plates 416, 418 to move within the housing 102.

In an alternative embodiment, the first and second interior volumes 412, 414 may be at least partially filled with a fluid selected to help control the movement of the first and second sliding plates 416, 418. For example, the fluid may comprise a compressible fluid, hydraulic fluid, magnetic fluid, lubricant, or the like that may be configured to be displaced by and flow around the first and second sliding plates 416, 418 when they move. The fluid may be selected according to a desired yield force which when exceeded will allow the first and second sliding plates 416, 418 to move.

The upper pole 104 may be used to couple the housing 102 to the structure 108. The upper pole 104 may comprise any suitable device capable of suspending a weight from an overhead structure such as a tube, pipe, column, or like member. In one embodiment, the upper pole 104 may comprise a rigid member fixedly coupled to the structure 108 at a first end and coupled to the first sliding plate 416 on a second end. The upper pole 104 may be coupled at either end by any suitable method. For example, the first end of the upper pole 104 may comprise or otherwise be attached to a mounting plate 202 that is bolted to the structure 108 thereby fixing the upper pole 104 in place. The second end of the upper pole 104 may be welded to the first sliding plate 416 such that the housing 102 may move with respect to the fixed upper pole 104.

The lower pole 106 may be used to couple the housing 102 to the equipment 314, 316. The lower pole 106 may comprise any suitable device capable of suspending a weight from the housing 102 such as a tube, pipe, column, or like member. In one embodiment, the lower pole 106 may comprise a rigid member coupled to the second sliding plate 418 at a first end and coupled to the boom 310, 312 at a second end. The first end of the lower pole 106 may be welded to the second sliding plate 418 such that the lower pole 106 and the housing 102 may independently move with respect to each other.

The lower pole 106 may comprise an extendible end portion 112 configured to allow a height of the equipment 314, 316 to be selectively adjusted. The extendible end portion 112 may comprise any suitable device or system for allowing a length of the lower pole 106 to be adjusted. For example, in one embodiment, the extendible end portion 112 may comprise an inner tube configured to fit within an outer, wherein each respective tube comprises a series of holes spaced along the length of the tubes. The holes may be configured to receive a pin, bolt, or other device such that an amount that the inner tube extends from the outer tube may be adjusted. In an alternative embodiment, the inner and outer tubes may comprise a set of mating threads configured to allow the inner tube to be screwed into the outer tube to a desired depth.

These and other embodiments for methods of isolating equipment from structural vibrations may incorporate concepts, embodiments, and configurations as described with respect to embodiments of apparatus for absorbing, isolating, and decoupling mounted equipment from a structure as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

The invention claimed is:

1. A mount for suspending equipment from a structure, comprising:
 a housing, comprising:
  an annular upper plate having a first open center portion;
  a first ring coupled to a lower surface of the upper plate;
  a middle plate coupled to the first ring to form a first interior volume defined by the lower surface of the upper plate, the first ring, and an upper surface of the middle plate;
  a first sliding plate received within the first interior volume and configured to allow the upper plate and the middle plate to slide with respect to the first sliding plate in a 360 degree range of motion limited by at least one of an inner diameter of the first open center portion and an inner diameter of the first ring;
  a second ring coupled to a lower surface of the middle plate;
  an annular lower plate having a second open center portion, wherein the lower plate is coupled to a lower surface of the second ring to form a second interior volume defined by an upper surface of the lower plate, the second ring, and a lower surface of the middle plate; and
  a second sliding plate received within the second interior volume, wherein the second sliding plate is configured to slide within the second interior volume with respect to the lower plate and the middle plate in a 360 degree range of motion limited by at least one of an inner diameter of the second open center portion and an inner diameter of the second ring;
 an upper pole coupled to the first sliding plate and extending upwardly through the first open center portion and configured to be coupled to the structure; and
 a lower pole coupled to the second sliding plate and extending downwardly through the second open center portion and configured to be coupled to the equipment.

2. A mount according to claim 1, wherein an upper and lower surface of the first sliding plate comprises a coating configured to control a coefficient of friction between:
   an upper surface of the first sliding plate and the lower surface of the annular upper plate; and
   a lower surface of the first sliding plate and the upper surface of the middle plate.

3. A mount according to claim 2, wherein the coating comprises a fluoropolymer.

4. A mount according to claim 2, wherein the coating is configured to provide a coefficient of friction sufficient to require a force of at least twice a weight of the equipment before the upper plate and the middle plate to slide with respect to the first sliding plate.

5. A mount according to claim 1, wherein an upper and lower surface of the sliding plate comprises a coating configured to control a coefficient of friction between:
   the upper surface of the second sliding plate and the lower surface of the middle plate; and
   the lower surface of the second sliding plate and the upper surface of the lower plate.

6. A mount according to claim 5, wherein the coating comprises a fluoropolymer.

7. A mount according to claim 1, wherein:
   a lower surface of the upper plate comprises a first coating configured to control a coefficient of friction between the upper plate and the first sliding plate;
   the upper surface of the middle plate comprises a second coating configured to control a coefficient of friction between the middle plate and the first sliding plate;
   the lower surface of the middle plate comprises a third coating configured to control a coefficient of friction between the middle plate and the second sliding plate; and
   an upper surface the lower plate comprises a fourth coating configured to control a coefficient of friction between the lower plate and the second sliding plate.

8. A mount according to claim 7, wherein each of first, second, third, and fourth coatings comprise a fluoropolymer.

9. A mount according to claim 1, wherein:
   the first open center portion comprises a diameter of between three and seven inches; and
   the second open center portion comprises a diameter of between three and seven inches.

10. A mount according to claim 1, wherein the lower pole comprises an adjustable extension arm configured to adjust a suspension height of the equipment.

11. A mount for suspending a piece of equipment from a structure, comprising:
   an annular upper plate having a first open center portion;
   a first ring coupled to a lower surface of the annular upper plate;
   a middle plate coupled to the first ring to form a first interior volume defined by the lower surface of the annular upper plate, the first ring, and an upper surface of the middle plate;
   a first sliding plate received within the interior volume, wherein the first sliding plate is configured to:
      allow the annular upper plate and the middle plate to slide with respect to the first sliding plate; and
      be coupled to the structure;
   a second ring coupled to a lower surface of the middle plate;
   an annular lower plate having a second open center portion, wherein the annular lower plate is coupled to a lower surface of the second ring to form a second interior volume defined by an upper surface of the annular upper plate, the second ring, and a lower surface of the middle plate; and
   a sliding plate received within the second interior volume, wherein the sliding plate is configured to:
      slide within the second interior volume with respect to the annular lower plate and the middle plate; and
      be coupled to the piece of equipment.

12. A mount according to claim 11, further comprising:
   an upper pole coupled to the first sliding plate and extending upwardly through the first open center portion, wherein the upper pole is configured to be coupled to the structure; and
   a lower pole coupled to the second sliding plate and extending downwardly through the second open center portion wherein the lower pole is configured to be coupled to the piece of equipment.

13. A mount according to claim 12, wherein the lower pole comprises an adjustable extension arm configured to adjust a suspension height of the equipment.

14. A mount according to claim 11, wherein:
   an upper and lower surface of the first sliding plate comprises a coating; and
   an upper and lower surface of the second sliding plate comprises a second coating.

15. A mount according to claim 14, wherein the first and second coatings comprise a fluoropolymer.

16. A mount according to claim 11, wherein:
   a lower surface of the upper plate comprises a first coating configured to control a coefficient of friction between the upper plate and the first sliding plate;
   the upper surface of the middle plate comprises a second coating configured to control a coefficient of friction between the middle plate and the first sliding plate;
   the lower surface of the middle plate comprises a third coating configured to control a coefficient of friction between the middle plate and the second sliding plate; and
   an upper surface the lower plate comprises a fourth coating configured to control a coefficient of friction between the lower plate and the second sliding plate.

17. A mount according to claim 16, wherein each of first, second, third, and fourth coatings comprise a fluoropolymer.

18. A mount according to claim 11, wherein:
   the first open center portion comprises a diameter of between three and seven inches; and
   the second open center portion comprises a diameter of between three and seven inches,
   wherein each of the first and second open center portions are configured to allow 360 degree range of motion limited of the first and second sliding plates.

* * * * *